United States Patent [19]
Cavotta et al.

[11] Patent Number: 5,908,556
[45] Date of Patent: Jun. 1, 1999

[54] AUTOMATIC IONIC CLEANLINESS TESTER

[76] Inventors: David A Cavotta, 5589 Lake Knoll Way, Noblesville, Ind. 46060; Michael C Huggins, 1405 Conti La., Kokomo, Ind. 46902; Kristine R Bewley, 6964 N. 400 West, Sharpsville, Ind. 46068

[21] Appl. No.: 08/876,288

[22] Filed: Jun. 16, 1997

Related U.S. Application Data

[62] Division of application No. 08/684,956, Jul. 19, 1996, Pat. No. 5,730,866.

[51] Int. Cl.$^6$ .................................................. B01D 15/08
[52] U.S. Cl. ...................... 210/656; 210/143; 210/198.2; 73/61.52; 73/61.55; 436/52; 436/150; 436/161
[58] Field of Search ........................... 422/62, 70, 82.01, 422/82.02, 82.03; 134/2; 210/635, 656, 659, 143, 181, 198.2; 73/61.52, 61.53; 436/52, 161, 150

[56] References Cited

U.S. PATENT DOCUMENTS

| | | | |
|---|---|---|---|
| 3,923,460 | 12/1975 | Parrott et al. | 23/230 |
| 4,265,634 | 5/1981 | Pohl | 23/230 |
| 4,472,354 | 9/1984 | Passell et al. | 422/62 |
| 4,628,726 | 12/1986 | Heikkila et al. | 73/61.1 |
| 4,679,428 | 7/1987 | Miller, Jr. et al. | 73/61.1 |
| 4,694,682 | 9/1987 | Heikkila et al. | 73/61.1 |
| 4,715,216 | 12/1987 | Muller | 73/61.1 |
| 4,732,686 | 3/1988 | Small et al. | 210/656 |
| 4,861,555 | 8/1989 | Mowery, Jr. | 422/70 |
| 4,991,428 | 2/1991 | Heyde | 73/61.1 |
| 5,042,293 | 8/1991 | Heyde | 73/61.1 |
| 5,044,509 | 9/1991 | Bristol | 148/23 |
| 5,244,000 | 9/1993 | Stanford et al. | 134/95.1 |
| 5,436,166 | 7/1995 | Ito et al. | 436/161 |
| 5,531,106 | 7/1996 | Lyon et al. | 73/61.56 |

*Primary Examiner*—Ernest G. Therkorn

[57] ABSTRACT

An automatic ion residue monitoring and testing system that has a particular application to quantify ionic residue on a printed circuit board. The monitoring system is a stand-alone unit that includes a purification system for providing deionized water. Deionized water from purification system is heated and sent to an extraction tank where it is held in a controlled quantity. A printed circuit board is placed in the extraction tank and the heated deionized water is caused to circulate through the extraction tank so as to remove ionic contamination on the circuit board. The system then automatically extracts a controlled quantity of now ionized water from the extraction tank and sends it to an ion chromatograph. The ion chromatograph tests the contaminated water, and provides a readout of the level of ionic contamination in the water.

5 Claims, 2 Drawing Sheets

AUTOMATIC IONIC CLEANLINESS TESTER

This is a division of application Ser. No. 08/684956 filed on Jul. 19, 1996, now U.S. Pat. No. 5,730,866.

BACKGROUND OF THE INVENTION

1. Field of the Invention

This invention relates generally to a system and method for automatically determining the concentration of contaminants and, more particularly, to a system and method for providing automatic quantification of critical ionic species on a printed circuit board, printed circuit board assembly following cleaning or a no-clean wave soldering process.

2. Discussion of the Related Art

High capacity manufacturing processes that rapidly produce a large number of printed circuit board (PCB) assemblies generally include machines that attach the electrical components onto the PCB, and machines that later solder the components in place on the board. After the electrical components have been positioned on the PCB assembly, but prior to the PCB assembly being subjected to the soldering step, a flux is applied to the PCB assembly by a flux application apparatus within a soldering machine. Such soldering machines may take on many different forms, such as wave fluxing or foaming machines, open spray fluxing machines, or mist systems. The soldering flux cleans the conductive traces on the PCB assembly in order to improve intermetallic bonding, and thus provide better electrical connections.

Traditional fluxes were generally resin based fluxes that sometimes left residues and contaminated the PCB assembly. Modern fluxes are generally either alcohol based or water based, where the alcohol or water makes up about 95% or more of the flux solution. The remaining 5% or less of the flux solution is a suitable acid and/or other chemicals depending on the particular flux application. For discussion of a particular low residue soldering flux of this type, see for example U.S. Pat. No. 5,004,509 issued Apr. 2, 1991 to Bristol.

With the traditional resin based fluxes, the PCB assembly was generally required to be cleaned following the soldering process to remove flux residue that may contaminate the PCB assembly and affect its operation, particularly the interconnection of the electronic components. With alcohol or water based fluxes, it was not necessary to clean the PCB assembly to remove flux residue because the majority of the flux would evaporate, and the residues would be small. However, evaporation of the fluxes on the PCB assembly does leave behind some residue, some or most of which may be ionic in nature. What is meant by ionic is that the residues may be conductive. Various ionic residue of this type are known in the art.

These ionic residues can have a harmful affect on the operation of the PCB assembly. Particularly, the ionic residue on the PCB assembly can cause electron migration across signal traces on the PCB assembly, resulting in a transfer of charge that is unintentional. Such a transfer of charge may ultimately reduce the useful life of the device, thus affecting its reliability. Other, more serious problems can also occur, such as component failure as a result of this ionic residue.

Currently, a manual process is used to quantify the ionic residue on a PCB assembly in order to monitor the PCB manufacturing process to control such residue. One known testing method is referred to as extraction, and includes the process of bringing loosely bound ionic contaminates into a solution of a known volume of deionized water. Particularly, a PCB assembly is removed from the process line, and placed in a Kpak bag, known to those skilled in the art. A graduated cylinder is used to measure a known volume of deionized water, and the measured quantity of water is placed in the Kpak bag. The Kpak bag is then placed in a hot water bath for a predetermined period of time so as to cause the ionic residue on the PCB assembly to be removed and dissolved in the water. A syringe is then used to extract a certain amount of a water sample from the Kpak bag and manually inject the sample volume into an ion chromatograph such as the DX-100 Ion Chromatograph, commercially available from Dionex of Sunnyvale, Calif., for analysis. The analysis process includes injecting the solution from the Kpak bag into a lour loc fitting located on a front panel of the ion Chromatograph. AI-450 software is used to control the operation of the ion chromatograph. After inputting a sample name and a dilution factor, the operator initiates the analysis cycle by invoking a start command. The ion chromatograph then gives the quantification of the constituent matter in the solution which can then be correlated to a specific amount of contamination per unit area on the PCB assembly.

In order to compare the solution to a reference so as to determine the ionic constituent residue, the system must be calibrated at start up, and whenever new eluent is added to the ion chromatograph. The calibration frequency is directly related to use, and is typically performed on a weekly basis. Generally, system calibration requires three successive runs with a known calibration standard.

A known calibration sequence for the testing system is given as follows. First, a volumetric flask for each calibration point is obtained, and each flask is filled with deionized water to about one-half of its total volume. Then, a desired volume of a known calibration standard is added to each flask, and the remaining volume of the flask is filled with the deionized water to obtain three final solutions of known concentrations. After the calibration standards are prepared, three successive sample runs using the calibration standards are performed. Following the successive calibration runs, the calibration is checked for linearity with a Calplot program that tests the linearity between each level of calibration. This relationship is calculated for each ion, and the calibration where all values are above 0.999 are deemed acceptable.

As is apparent from the above description, the known process for determining the quantity of ionics reside on a PCB assembly is not well suited to the manufacturing floor. This is because the above described process is very operator interactive and requires a higher than normal amount of training and responsibility. The calibration is complex and critical, and is generally outside the scope of operator responsibilities. Also, manual sample volume measurements and calibration standard mixing draws immediate question to the accuracy and repeatability of the process. The AI-450 software interface used in the control of the operation of the ion chromatograph is structured for a laboratory environment, and requires a higher than normal level of computer literacy.

What is needed is a method and apparatus for determining the quantity of ionic residue on a PCB assembly that is relatively easy to use and is capable of being performed on the manufacturing floor near the PCB assembly stations. It is therefore an object of the present invention to provide such a process and apparatus.

SUMMARY OF THE INVENTION

In accordance with the teachings of the present invention, an automatic ion residue monitoring and testing system is disclosed that has a particular application to quantify ionic residue on a printed circuit board. The monitoring system is a stand-alone unit that is computer controlled to automatically provide the testing and calibration processes. The system includes a purification system for providing deionized water. Deionized water from the purification system is heated and sent to an extraction tank where it is held in a controlled quantity. A printed circuit board is placed in the extraction tank and the heated deionized water is caused to circulate through the extraction tank so as to remove ionic contamination on the circuit board. The system then automatically extracts a controlled quantity of now ionized water from the extraction tank and sends it to an ion chromatograph. The ion chromatograph tests the contaminated water, and provides a readout of the level of ionic contamination per unit area on the printed circuit board.

The system further causes an automatic calibration to be performed where controlled amounts of a calibration standard from a storage tank and a controlled amount of deionized water are mixed and sent to the ion chromatograph at desirable times to calibrate the chromatograph for subsequent sample analysis. The system provides for various automatic rinsing and purging cycles of the plumbing lines, valves, and tanks associated with the monitoring system.

Additional objects, advantages, and features of the present invention will become apparent from the following description and appended claims, taken in conjunction with the accompanying drawings.

DETAILED DESCRIPTION OF THE PREFERRED EMBODIMENTS

The following discussion of the preferred embodiments directed to an automatic ionic cleanliness tester for monitoring ionic residue on a printed circuit board is merely exemplary in nature and is in no way intended to limit the invention or its applications or uses.

Figure 1:
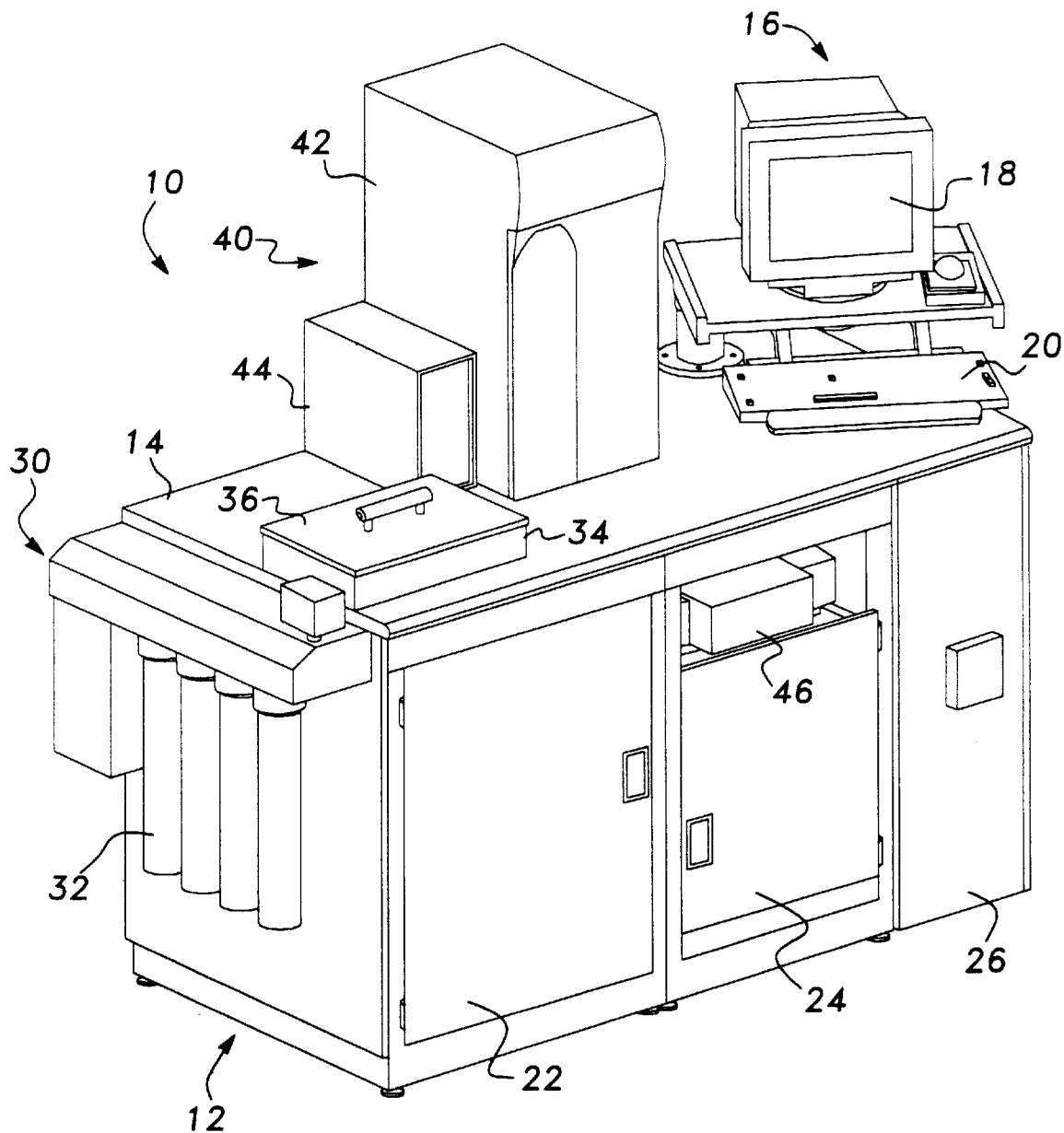
FIG. 1 is a plan view of an automatic cleanliness test system according to an embodiment of the present invention.

FIG. 1 shows an overview diagram of an automatic cleanliness test system 10 according to an embodiment of the present invention. The system 10 has particular application for determining ionic residue on a printed circuit board. However, the system 10 has many other applications beyond that particular use. The system 10 includes various components and units supported on and within a support structure assembly 12 including a table top 14. The system 10 is controlled by a suitable 1computer system 16, such as a Gateway PC, including a computer screen 18 and a keyboard 20. A specialized I/O board (not shown) is added to the computer system 16 to control the various valves, pumps, heaters, etc., as described below. Suitable computer software is provided for interfacing purposes to automatically perform these functions.

The support structure assembly 12 includes an enclosed cabinet portion 22 that houses the various plumbing fixtures and connections of the system 10, an enclosed cabinet portion 24 that houses various electrical systems of the system 10, and an enclosure cabinet portion 26 that houses electrical control circuitry for the main power distribution used to operate the system 10. The electrical systems within the cabinet portion 24 include a suitable relay board that receives instructions from the computer system 16, and transfers electrical signals to operate the various valves and pumps described below.

The system 10 includes a purification system 30 that receives processed pretreated tap water and purifies the tap water for deionization purposes. The purification system 30 includes various replaceable filters 32 that perform the deionization. In one embodiment, the purification system 30 is the E-pure system commercially available from Barnsted of Dubuque, Iowa, however, the purification system 30 can be any suitable deionization system known to those skilled in the art suitable for the purposes described herein. An extraction tank 34 is positioned in the table top 14, and is connected to the purification system 30 and the plumbing system of the system 10 to receive and hold deionized water from the purification system 30. The tank 34 includes a lid 36 that is removable by an operator, so that a PCB to be tested can be inserted in the tank 34 to allow the ionic residue on the PCB to be dissolved in the water. An ion chromatography system 40, including an ion chromatograph 42 and an interface system 44, is provided to do an ionic analysis on the water in the extraction tank 34 after the PCB has soaked in the tank 34 for a predetermined period of time. In one embodiment, the system 40 is the DX-100, or other models, Ion Chromatograph available from Dionex, but can be any type of chromatography system suitable for the purposes described herein.

As will be discussed in detail below, a carefully measured amount of heated deionized water is added to the extraction tank 34, and a PCB assembly is then placed in the tank 34. Contaminated ionized water is then sampled from the tank 34 and analyzed by the chromatography system 40. The computer system 16 interfaces with the interface system 44 so that a reading of the ionic constituents in the contaminated water is determined. A printout of the contamination level is provided by a printer 46.

Figure 2:
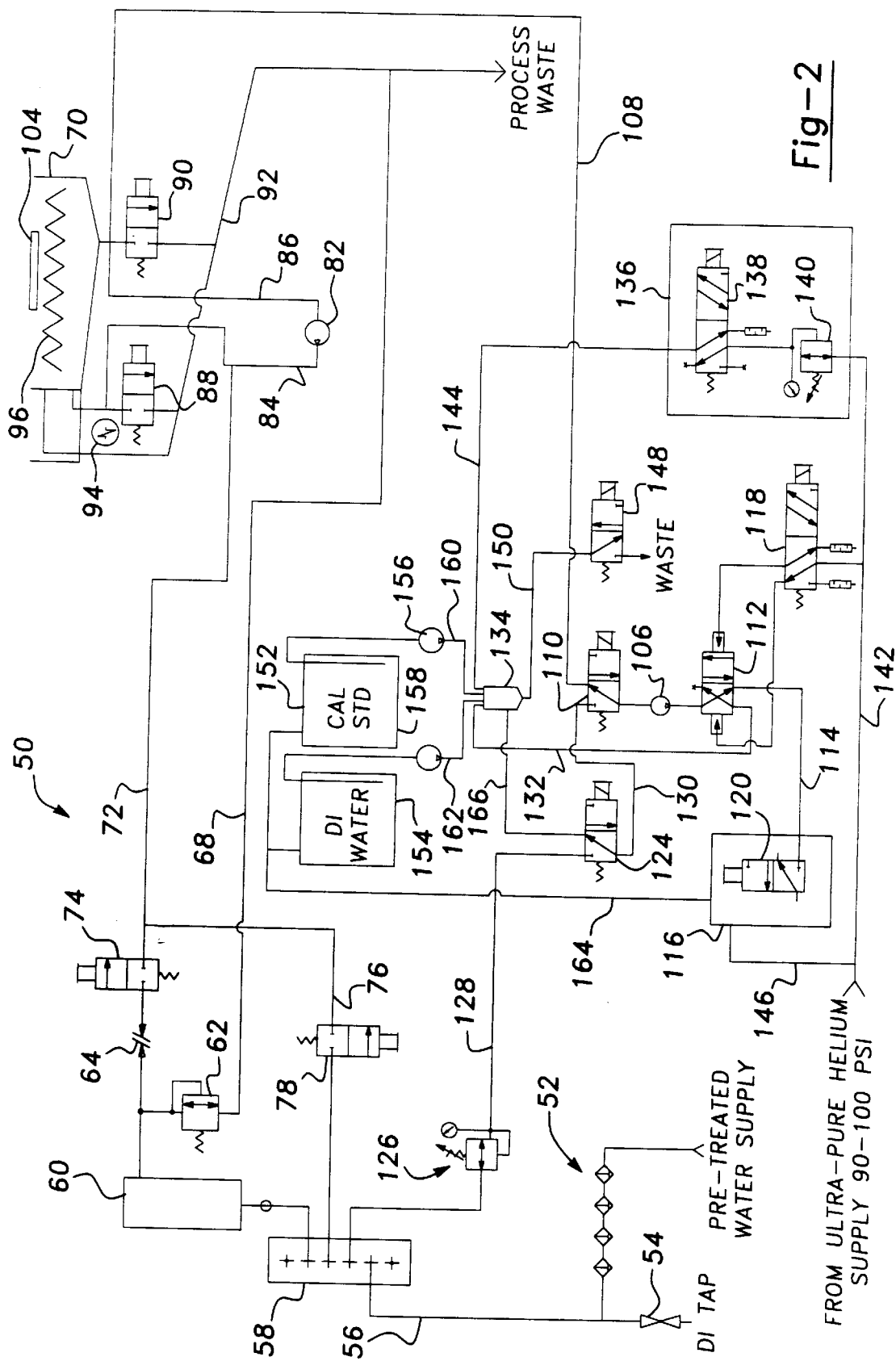
FIG. 2 is a schematic diagram of the operation of the automatic cleanliness tester of FIG. 1.

A schematic diagram 50 of the plumbing fixtures and connections of the cleanliness testing system 10 is shown in FIG. 2. An input of pretreated water is connected to a purification system 52 representing the purification system 30. The purification system 52 filters the supply water to have a predetermined resistivity suitable for the purposes of the present invention. A water tap 54 allows deionized water to be extracted from a water line 56 after the water supply is purified by the system 52. The deionized water is sent to a manifold 58 through the line 56 to separate and distribute the deionized water through various plumbing lines in the system 10, as will be discussed in detail below. One line from the manifold 58 is connected to an in-line heater 60 that heats the deionized water to, for example, 180° F. An output of heated water from the in-line heater 60 is applied to a pressure relief valve 62 and a flow control valve 64. The flow control valve 64 controls the flow of heated water from the heater 60. The pressure relief valve 62 is a safety device that allows the heated water to be dumped to waste through a water line 68 in the event that the heater 60 heats the water too high creating excess pressure. When desired, heated deionized water from the heater 60 is sent to a sample tank 70 through a water line 72 by electrically activating an actuator valve 74. Likewise, cool deionized water from the manifold 58 is sent to the sample tank 70 through a water line 76 and the line 72 by activating an actuator valve 78.

The sample tank 70 represents the extraction tank 34 discussed above. Prior to the PCB being introduced into the sample tank 70, the sample tank 70 is rinsed and purged several times, and then filled to a known and tightly controlled level of heated deionized water. A recirculation pump 82 is provided to recirculate water in the tank 70 through lines 84 and 86 during rinsing and when the PCB is in the tank 70. Two actuator valves 88 and 90 allow water in the tank 70 to be removed from the tank 70 to waste, as will be described below. To perform the rinsing and purging process, both of the valves 74 and 78 are opened to allow the fastest rate of water available to flow through the line 72 into the line 84 to fill the tank 70. At this time, both the valves 88 and 90 are closed. An overflow line 92 prevents the tank 70 from overflowing by removing overflow water to waste. While the tank 70 is filling the recirculation pump 82 is activated in order to cause water to recirculate through the lines 84 and 86 and the tank 70. When the tank 70 is full, the valves 74 and 78 are closed. After a predetermined period of time, the pump 82 is turned off and the valves 88 and 90 are opened to drain the tank 70 to waste on the line 92. This process is performed a number of times until the tank 70 and the lines 84 and 86 are clean.

The tank 70 is then filled with heated water by opening the valve 74 and keeping the valve 78 closed. A temperature sensor 94 monitors the temperature of the deionized water flowing into the tank 70. The tank 70 is filled to a level near the overflow level, and then the valve 74 is closed. The valve 88 is then opened to drain some of the deionized water out of the tank 70 so that a tightly controlled known quantity of deionized water is present in the tank 70 for purposes of the test. The volume of the tank 70 can be tailored to particular product families so as to insure maximum instrument sensitivity, accuracy and repeatability. The valve 88 is then closed, and the recirculation pump 82 is switched on. A heater 96 within the tank 70 keeps the deionized water in the tank 70 at the desirable temperature.

A PCB assembly 104 is then inserted into the tank 70, and held in there for a predetermined period of time, for example 10 minutes, so as to allow contaminant material on the PCB assembly 104 to be dissolved in the deionized water in the tank 70. After the preset dissolving time has expired, an injection pump 106 is activated to pump a controlled quantity of the now ionized water within the tank 70 through a sample line 108, an actuator valve 110, a pilot valve 112 and a sample line 114 into an ion chromatograph 116. The ion chromatograph 116 represents the ion chromatograph 42, above. The valve 112 is a pilot valve actuated by air pressure, and is controlled by an actuator valve 118. The valves 110 and 112 are in their default position when the sample is introduced into the ion chromatograph 116. The ion chromatograph 116 operates in the same manner as that of the manual system of the prior art discussed above after being started through ACT software, and therefore need not be discussed here. Through the software associated with the computer system 16 and the interface system 44, the ion chromatograph 116 automatically performs the process described above after an operator run command so as to provide an indication of the ionic contamination in the water from the tank 70 to be output by the printer 46 and read by an operator. The command is initiated at the beginning of the entire process. The ion chromatograph 116 starts automatically when it is time without further operator intervention. A valve 120 allows the ion chromatograph 116 to be switched to a manual sample injection.

At the same time that the ion chromatograph 116 is analyzing the sample from the tank 70, the tank 70 is rinsed and purged to waste through the valves 88 and 90, and cleaned in the manner as described above for the next sample. Thus, the system 10 will simultaneously be cleaning the tank 70 and refilling it with deionized water while the ion chromatograph 116 is performing the analysis. A plurality of consecutive tests can be done on a single PCB assembly left in the tank 70 or multiple PCB assemblies taken from the same location in the assembly line to give an indication of ionic contamination at any given time.

Prior to the ion chromatograph 116 performing the analysis of the sample in the tank 70, the ion chromatograph 116 needs to be calibrated against a calibration standard having a known amount of ions to give accurate results. Prior to calibrating the ion chromatograph 116, the tanks, valves and flow lines used in the calibration process must be cleaned and purged. To perform this cleaning process, the injection pump 106, an actuator valve 124, valves 110 and 112 are appropriately activated by the system 10 so that deionized water from the manifold 58 flows through a pressure regulator 126 and travels through water lines 128, 130 and 132 into an injection chamber 134. To allow this flow, each of the valves 110, 112 and 124 are electrically actuated from their default position by the system 10. When the injection chamber 134 is full or is filling, a valve assembly 136 is actuated in order to allow helium under pressure to flow through a valve 138 and a pressure regulator 140 in the assembly 136 to the injection chamber 134 through lines 142 and 144. Helium at a pressure of 90–100 PSI is necessary for the operation of the ion chromatograph 116, and is applied to the ion chromatograph 116 on line 146. The pressure regulator 140 reduces the helium pressure to a lower pressure to blow out the injection chamber 134. By activating a valve 148, the deionized cleaning water in the injection chamber 134 is flushed to waste through line 150. The valves 110, 112, 124, and the injection chamber 134 are flushed and purged in this manner so that they are clean for subsequent calibration or analysis.

For the calibration sequence, a tank 152 is provided that includes a calibration standard having a very precise level of contaminants. Additionally, a tank 154 is provided of a deionized water generally taken from the tap 54. A calibration pump 156 and a deionized water pump 158 are activated by the system 10 so that a controlled amount of the calibration standard and the deionized water from the tanks 152 and 154, respectively, are applied on lines 160 and 162 to the injection chamber 134. The pumps 156 and 158 are tightly controlled so that each revolution of the pumps 156 and 158 injects a controlled amount of fluid into the injection chamber 134 for mixing. Pumps of this type are generally controlled by electrically actuating a stepper motor. Commercially available pumps that provide this level of accuracy are available, for example from Fluid Metering, Inc. A line 164 of helium is applied to the tanks 152 and 154 from the ion chromatograph 116 at about 15 PSI in order to keep bubbles out of the tanks 152 and 154 and prime the pumps 156 and 158. The software of the system 10 is programmed to provide the appropriate number of revolutions of the pumps 156 and 158 to provide the mixture of the calibration standard and the deionized water to a desirable standard. In one embodiment, three calibration processes are performed at varying levels of ion contamination to provide a more accurate calibration for these samples. Each of the valves 110, 112, and 124, and the injection pump 106 are activated such that the solution in the injection chamber 134 flows from the injection chamber 134 through line 166 and the lines 130, and 114 into the ion chromatograph 116. This calibration is performed for different levels of contaminant to get a range for calibration purposes.

To automatically perform the operations as discussed above, the system 10 is provided with appropriate software as the link between the operator and the system 10. This software controls the testing sequence and all associated hardware, including filling, rinsing, extracting, calibration, etc. Further, the software is responsible for managing all relevant, product specific, data needed to perform the tests. This task accomplished through a data base that prompts the operator upon initial testing and stores the information for subsequent testing. Further, the software interface provides a user friendly environment, supported by menu selectable help topics, which step the operator through all necessary functions associated with analyzing circuit board assemblies and system calibration.

The various plumbing lines discussed above can be many different types of plumbing lines suitable for the purposes described herein. For example, the line 92 can be 1" inner diameter (ID) reinforced PVC tubing, the lines 56, 72, 68, 76, 84 and 86 can be ⅜" ID reinforced PVC tubing, the lines 108, 128, 130, 150, 160 and 162 (on the suction side of the pumps 156 and 158) can be ⅛" outer diameter (OD) by 1/16" ID tefzel tubing, the lines 114 and 132 can be 1/16" OD by 0.020" ID peek tubing, the lines 142, 144 and 146 can be ⅛" OD by 1/16" ID urethane tubing, and 1/16 OD by 0.010 ID tefzel tubing can be used at various locations such as for lines 160, 162 on the pressure side of the pumps 156 and 158 in the plumbing. Also, the electrical connections required to activate the different valves, pumps, heaters, etc., discussed above, as controlled by the computer system 16, would be well apparent to one of ordinary skill in the art from the discussion above. Further, AI-450 operating software can be used in conjunction with the interface system 44 to perform the various tasks as discussed above.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

The embodiments of the invention in which an exclusive property or privilege is claimed are defined as follows:

1. A method for automatically determining the level of contamination of a solution, said method comprising the steps of:
   providing a supply of purified water;
   providing a controlled quantity of the purified water to a sample tank through a plumbing system;
   soaking an article in the sample tank so as to dissolve residue on the article in the purified water in the sample tank;
   providing a chromatographic analyzing device that receives contaminated water sample from the sample tank and ion analyzes the water to determine the level of contamination in the water; and
   providing a control device that automatically causes the plumbing system to fill the sample tank and send the water sample to the analyzing device.

2. The method according to claim 1 wherein the step of providing a supply of purified water includes the step of deionizing the water to remove ions from the water.

3. The method according to claim 1 wherein the step of providing an analyzing device includes providing an ion chromatograph that analyzes the water sample to determine the level of ions in the water sample.

4. The method according to claim 1 further comprising the steps of providing a calibration tank holding a quantity of a known calibration standard, said step of providing a control device includes providing a control device that automatically causes the plumbing system to extract the calibration standard from the calibration tank and send it to the analyzing device to be analyzed.

5. The method according to claim 1 wherein the step of soaking an article in the sample tank includes soaking a printed circuit board assembly in the sample tank so as to dissolve ionic residue on the printed circuit board assembly into the water in the sample tank.

* * * * *